US00PP23931P2

(12) United States Plant Patent
Williams

(10) Patent No.: US PP23,931 P2
(45) Date of Patent: Sep. 24, 2013

(54) ***CANNA* PLANT NAMED 'MAUI PUNCH'**

(50) Latin Name: *Canna×generalis*
Varietal Denomination: Maui Punch

(75) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 41 days.

(21) Appl. No.: 13/506,027

(22) Filed: Mar. 21, 2012

(51) Int. Cl.
*A01H 5/00* (2006.01)

(52) U.S. Cl.
USPC ..... Plt./415

(58) Field of Classification Search
USPC ..... Plt./415
See application file for complete search history.

*Primary Examiner* — Kent L Bell
(74) *Attorney, Agent, or Firm* — Penny J. Aguirre

(57) ABSTRACT

A new cultivar of *Canna* plant named 'Maui Punch', that is characterized by its medium to large flowers that are bright yellow with numerous bright red spots that are self-cleaning and do not require deadheading, its compact plant habit, its branched flower spikes, resulting in numerous flowers per spike, and light green foliage, and its bloom from spring until frost.

2 Drawing Sheets

Botanical classification: *Canna×generalis.*
Cultivar designation: 'Maui Punch'.

BACKGROUND OF THE INVENTION

The present invention relates to a new and distinct cultivar of *Canna×generalis* known as 'Maui Punch', and is hereinafter referred to as 'Maui Punch'.

The new cultivar was derived from a controlled breeding program conducted by the Inventor at his nursery in Louisville, Ky. The overall purpose of the breeding program is to make a selection of *Canna* with a dwarf, compact plant habit and flowers that were self-cleaning flowers with spotted coloration. 'Maui Punch' arose from a cross made in June of 2010 between 'Creation Sparks' (not patented) as the female parent and an unnamed plant of *Canna×generalis* as the male parent. 'Maui Punch' was selected as a single unique plant in August of 2010 from amongst the seedlings derived from the above cross.

Asexual reproduction of the new cultivar was first accomplished by root cuttings by the Inventor in Louisville, Ky. in September of 2010. Asexual reproduction of the new cultivar has shown that the unique features are stable and reproduced true to type in successive generations.

SUMMARY OF THE INVENTION

The following traits have been repeatedly observed and represent the characteristics of the new cultivar as grown in Louisville, Ky. These attributes in combination distinguish 'Maui Punch' as a new and unique cultivar of *Canna.*

1. 'Maui Punch' exhibits medium to large flowers that are bright yellow with numerous bright red spots.
2. 'Maui Punch' exhibits flowers that are self-cleaning and do not require deadheading.
3. 'Maui Punch' exhibits a compact plant habit; reaching 0.9 to 2.1 m in height.
4. 'Maui Punch' exhibits branched flower spikes, which results in numerous flowers per spike.
5. 'Maui Punch' exhibits light green foliage.

6. 'Maui Punch' has a vigorous and strong growth habit.
7. 'Maui Punch' blooms from spring until frost in Kentucky.

The female parent plant, 'Creation Sparks', differs from 'Maui Punch' in being much taller in height and in having flowers that are not self-cleaning and that are lighter yellow with orange spots. The male parent differs from 'Maui Punch' in having lighter yellow flowers that have orange to light red spots and in having a less vigorous growth habit. 'Maui Punch' can be most closely compared to the cultivars 'Phasion' (U.S. Plant Pat. No. 10,569 and 'Orange Punch' (not patented). Both are similar to 'Maui Punch' in having a vigorous growth habit and in flowering from spring until frost. 'Phasion' differs from 'Maui Punch' in being taller in height, in having multicolored foliage, in having flowers that are orange in color without spots and are not self-cleaning. 'Orange Punch' differs from 'Maui Punch' in being taller in height and in having orange flowers.

BRIEF DESCRIPTION OF THE DRAWING

The accompanying colored photographs illustrate the overall appearance and distinct characteristics of the new *Canna*. The photographs were taken of a 2 year-old plant as grown in a garden in Eustis, Fla.

Figure 1:
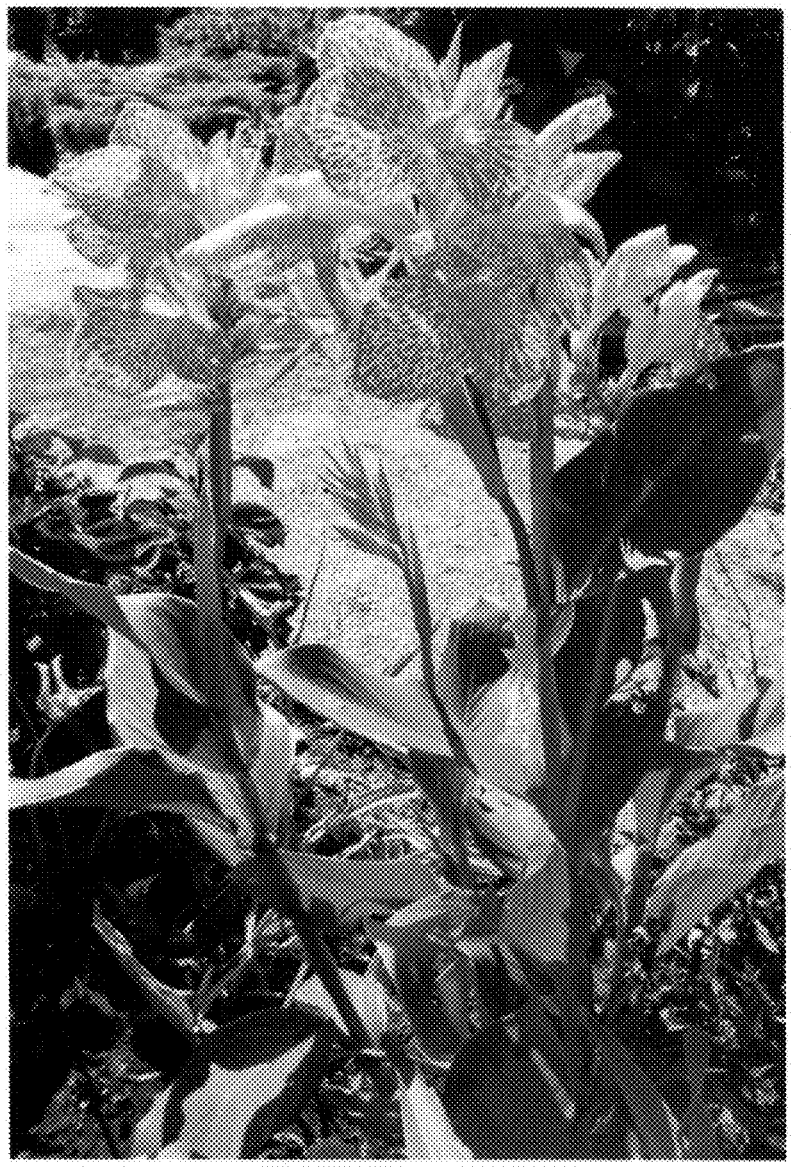
FIG. 1 provides a side view of a plant of 'Maui Punch' in bloom.
Figure 2:
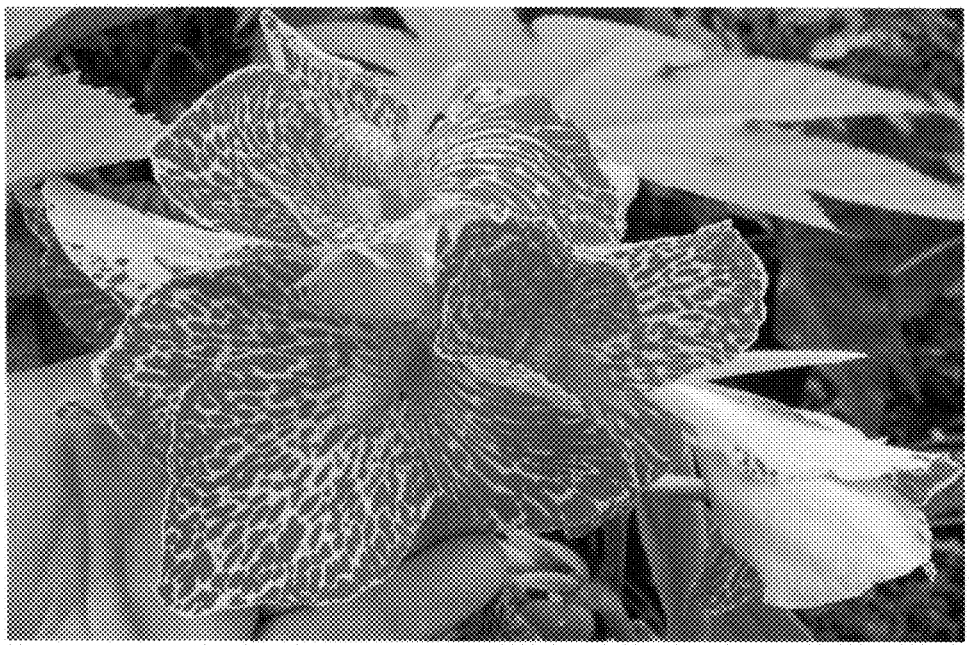

The photograph in FIG. 2 provides a view of an inflorescence of 'Maui Punch'.

Figure 3:
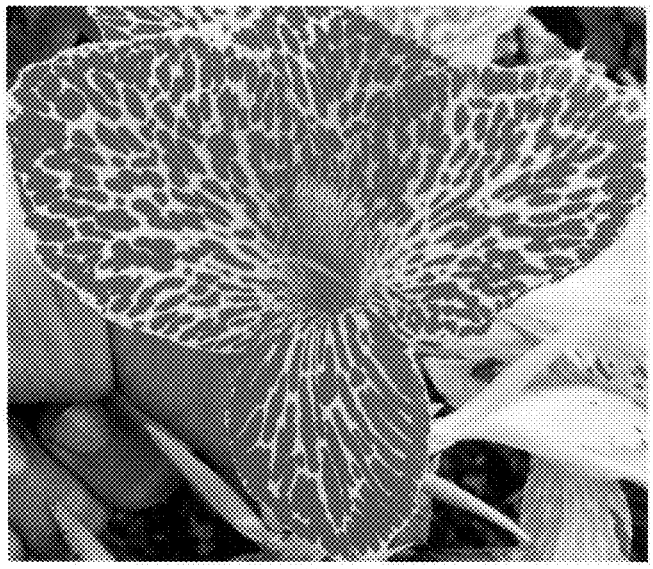

The photograph in FIG. 3 provides a close-up view of a flower of 'Maui Punch'. The colors in the photographs are as close as possible with the photographic and printing technology utilized and the color values cited in the Detailed Botanical Description accurately describe the colors of the new *Canna.*

DETAILED BOTANICAL DESCRIPTION OF THE PLANT

The following is a detailed description of two year-old plants of the new cultivar as grown outdoors in a greenhouse in Eustis, Fla. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

General description:

*Blooming period*.—About 18 weeks; from spring until frost in Kentucky.

*Plant type*.—Deciduous, tropical, perennial.

*Plant habit*.—Upright, dwarf, tufted leaves on stout stems.

*Height and spread*.—Reaches 0.9 to 1.2 m in height and 60 to 90 cm in width.

*Hardiness*.—U.S.D.A. Zones 7 to 11.

*Diseases and pests*.—No particular resistance or susceptibility to diseases and pests has been observed.

*Roots*.—Fleshy.

*Propagation type*.—In vitro propagation is preferred.

*Growth rate*.—Vigorous.

Stem description:

*Stem size*.—An average of 4.0 cm in length and an average of 1.5 cm in width (with sheaths).

*Stem type*.—Stout, surrounded by sheathed leaf petioles.

*Stem color*.—Inner stem 144A, stems are defined by color of outer petiole surface; 144A with stripes of 137B.

*Stem surface*.—Defined by outer petiole surface.

*New shoots*.—An average of 7 cm in length and 8 mm in width prior to leaf unfurling, 144A with stripes of 137B in color.

Foliage description:

*Leaf shape*.—Elliptic to slightly ovate.

*Leaf division*.—Simple.

*Leaf base*.—Cuneate to sheathed petiole.

*Leaf apex*.—Acuminate with small mucronate tip.

*Leaf venation*.—Pinnate, mature leaves; veins are raised on upper surface and recessed on lower surface, color matches leaf coloration except for mid rib; 137D on upper surface and 144B on lower surface.

*Leaf margins*.—Entire, very slightly wavy.

*Leaf attachment*.—Petiolate.

*Leaf arrangement*.—Alternate with petioles sheathed.

*Leaf surface*.—Glabrous on upper surface and lower surface with a slight sheen on both surfaces on newer leaves.

*Leaf orientation*.—Emerge upright and become nearly horizontal and slightly cascading downward when mature.

*Leaf color*.—New foliage, upper and lower surface; 137B, maturing foliage, upper and lower surface; 137B, fully mature foliage, upper and lower surface; 137A.

*Leaf size*.—Average of 25 cm in length and 14 cm in width when mature.

*Leaf quantity*.—An average of 7 per shoot 40 cm in length.

*Petioles*.—About 17 cm in length (sheathed to base with upper leaves the longest), an average of 1.5 cm in width, glabrous on inner and outer surface, sulcate and clasping to stem the entire length, color outer and inner surface; 144A with stripes of 137B.

Inflorescence description:

*Inflorescence type*.—Terminal branched raceme that elongates as individual flowers open; flowers with showy staminodes that are arranged spirally along the rachis and open sequentially during the bloom season.

*Inflorescence size*.—Average of 19 cm in length and 15 cm in diameter (dependant on number of blooms open).

*Flower buds*.—Oblong in shape, an average of 6 cm in length and 1 cm in width, a blend of 7A to 7D in color with light spots of 178C.

*Flower fragrance*.—None detected.

*Lastingness of inflorescence*.—Inflorescence blooms continuously during the bloom period, individual flowers last about 2 days.

*Flower quantity*.—Continuously produced throughout the bloom season, one to six open at one time on branched raceme, an average of 70 flowers produced in a season, about 20 buds present at one time.

*Flower type*.—Comprised of less showy sepals and petals and showy staminodes.

*Flower size*.—Average of 10 cm in diameter and depth.

*Rachis*.—Average of 10 cm in length (includes peduncle about 6 cm in length) and an average of 5 mm in width, an average of 2 branches; about 7 mm in length and 4 mm in width, color a blend of 144A and 137B, glabrous surface, shape is oval and becoming flattened on one side near apex, an average of 1 bract; an average of 10 cm in length and 2.5 cm in width, curled inward, oblong in shape, glabrous on both surfaces, clasping base, apex acuminate with small mucronate tip, a blend of 144A and 137B in color on both surfaces.

*Sepals*.—3, lanceolate in shape, truncate base, narrowly acute apex, about 1.8 cm in length and 6 mm in width, upper and lower surface 144B in color, glabrous on upper and lower surface, persist after staminodes drop.

*Petals*.—3, oblong in shape, truncate base, acute apex with mucronate tip, about 6 cm in length and 1 cm in width, glabrous on both surfaces, curled inward and held upright on mature flowers.

*Pedicels*.—Stout, 5 mm in length and width, glabrous surface, 144B in color.

*Staminodes*.—Sterile; 3, size; an average of 8 cm in length and 4 cm in width, obovate-elliptic in shape, apex round, base cuneate to narrower base about 2 cm in length and 7 mm in width with truncate base, margins very slightly crenate (irregular) and wavy, color upper and lower surface; upper surface 7A in color with spots 45B, lower surface 9A in color with spots 166C with rare spots of 45B, fertile male, 1, an average of 6.5 cm in length and 1.3 cm in width, renal-oblong in shape, apex acute with deep notch, base cuneate to a truncate base, margins entire, color upper surface; 45B in color with spots of 45B, glabrous on upper and lower surface, color lower surface 9A with spots of 166C fertile female; 1 staminode pistil, an average of 7 cm in length and 2.5 cm in width, upper surface 7A in color with spots 45B, lower surface 9A in color with spots 166C and rare spots of 45B, glabrous on upper and lower surface, broadly acute apex, truncate base.

Reproductive organs:

*Gynoecium*.—1 pistil, style is an average of 6 cm in length and 4 mm in width, narrowly oblanceolate in shape, narrow truncate base, margins smooth, color upper and lower surface; 15B in color with minute spots 166C, glossy on upper and lower surface, stigma surrounds apex, is about 2 mm in length and 7A in color, ovary is inferior, about 5 mm in length and 3 mm in width, and 146C in color.

*Androcoecium.*—1 stamen, about 4.5 cm in length, filament is adnate to edge of staminode, 7A in color, about 2.5 cm in length, anthers are about 1 cm in length, very slightly curved, 199D in color and basifixed, pollen is moderate in quantity and 202D in color.

*Fruit and seed.*—Capsule, globose, 147A in color, spiky surface, about 1.5 cm in length and width, seed formation was not observed.

It is claimed:

1. A new and distinct cultivar of *Canna* plant named 'Maui Punch' as herein illustrated and described.

* * * * *